United States Patent
Harris et al.

(10) Patent No.: US 7,800,756 B2
(45) Date of Patent: Sep. 21, 2010

(54) METHOD AND APPARATUS FOR ANALYZING COATINGS ON CURVED SURFACES

(75) Inventors: Geoffrey G. Harris, Midland (CA); Daniel B. Mitchell, Port McNicoll (CA); Douglas J. Brown, Midland, CA (US)

(73) Assignee: Raytheon Company, Waltham, MA (US)

( * ) Notice: Subject to any disclaimer, the term of this patent is extended or adjusted under 35 U.S.C. 154(b) by 260 days.

(21) Appl. No.: 12/170,075

(22) Filed: Jul. 9, 2008

(65) Prior Publication Data

US 2010/0007883 A1    Jan. 14, 2010

(51) Int. Cl.
*G01J 4/00* (2006.01)
(52) U.S. Cl. .................................................. 356/369
(58) Field of Classification Search ............... None
See application file for complete search history.

(56) References Cited

U.S. PATENT DOCUMENTS

| 5,936,726 | A  | * | 8/1999 | Takeda et al. ............ 356/237.2 |
| 6,687,002 | B2 | * | 2/2004 | Stehle et al. ................ 356/369 |

* cited by examiner

*Primary Examiner*—Tu T Nguyen
(74) *Attorney, Agent, or Firm*—Haynes and Boone, LLP

(57) ABSTRACT

An ellipsometer is used to analyze each of a plurality of sample portions that each include a substrate portion with a coating portion thereon, the substrate portions corresponding to respective spaced portions of a part with a curved surface. For each sample portion, the analysis includes: directing onto the coating portion a beam of radiation that includes first and second components with different polarizations; detecting energy of each of the first and second components reflected by the sample portion; and generating data that includes, for each of a plurality of different wavelengths, information regarding a change caused by the sample portion to a relationship between the first and second components.

12 Claims, 3 Drawing Sheets

METHOD AND APPARATUS FOR ANALYZING COATINGS ON CURVED SURFACES

FIELD OF THE INVENTION

This invention relates in general to analysis of coatings and, more particularly, to analysis of coatings on curved surfaces.

BACKGROUND

When fabricating optical components such as lenses, a coating is often formed on a surface of the component, to provide desired optical or physical properties. For example, the coating may provide an anti-reflective (AR) characteristic, a filtering characteristic, physical protection for the component, some other characteristic, or a combination of two or more characteristics. These coatings often include multiple layers of different materials that collectively provide the desired characteristic(s).

The layers in a coating should ideally have a uniform thickness, and the optical and mechanical characteristics of the layer should ideally be uniform throughout the layer. But as a practical matter, this is not always the case. For example, where a coating is formed on a relatively highly curved surface, it is common for a given layer within the coating to have a peripheral region that is as much as 30% to 50% thinner than a central region of that layer, or even more than 50% thinner. Further, different layers in the same coating often have different degrees of variation in thickness. For example, one layer may be 30% thinner in a peripheral region than in a central region, while another layer may be 50% thinner in the peripheral region that in the central region. Thus, even assuming that the layers of a coating all have the proper thicknesses in the central region, the thicknesses in the peripheral region will typically not be correct and, moreover, the ratios of thickness in the peripheral region will not be correct. As a result, the coating will provide the desired optical and mechanical characteristics in its central region, but may fail to provide these desired characteristics in its peripheral region, or may at least exhibit a degradation of these characteristics in the peripheral region.

One existing approach for analyzing a coating is to use a spectrophotometer to measure transmissivity and/or reflectance of the coating, at different locations on the coating. While existing approaches of this type have been generally adequate for their intended purposes, they have not been satisfactory in all respects.

BRIEF DESCRIPTION OF THE DRAWINGS

A better understanding of the present invention will be realized from the detailed description that follows, taken in conjunction with the accompanying drawing, in which.

DETAILED DESCRIPTION

Figure 1:
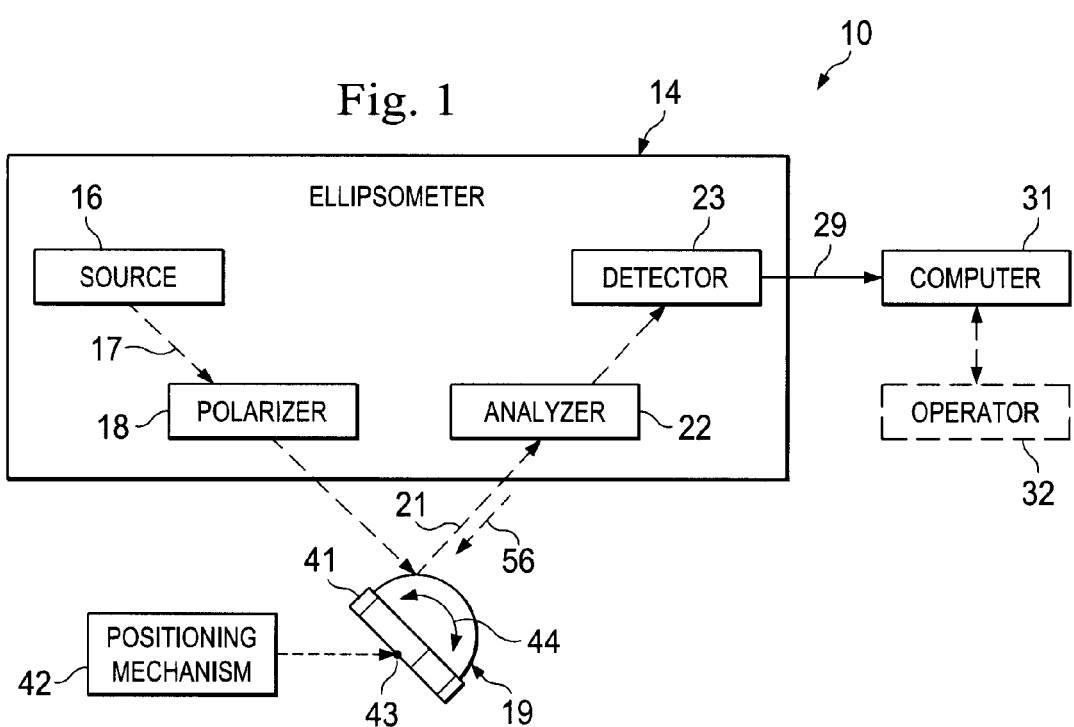
FIG. 1 is a block diagram of a coating analysis apparatus that embodies aspects of the invention, and shows an optical component that can be analyzed by the illustrated apparatus.

FIG. 1 is a block diagram of a coating analysis apparatus 10 that embodies aspects of the invention. The apparatus 10 includes an ellipsometer 14 of a known type. In the disclosed embodiment, the ellipsometer 14 is a model SOPRA GES5 ellipsometer obtained commercially from Sopra Inc. of Palo Alto, Calif. Alternatively, however, it would be possible to use any other suitable device.

Since the ellipsometer 14 is a device of a known type, it is described here only briefly, for the purpose of facilitating an understanding of the present invention. More specifically, the ellipsometer 14 includes a radiation source 16, and the source 16 emits radiation that propagates along a path 16, and passes through a polarizer 18. After leaving the polarizer 18, the radiation has two components with different polarizations. These two different polarizations are commonly referred to as "P" and "S" polarizations. In the disclosed embodiment, when these two components leave the polarizer, they have substantially the same amplitude and substantially the same wavelength (frequency), and are substantially in phase with each other.

The polarized radiation traveling along the path 17 impinges on an optical component 19. The component 19 is not part of the ellipsometer 14, and is discussed in more detail later. The component 19 reflects at least some of the polarized radiation from the ellipsometer. The reflected radiation travels along a path of travel 21 through an analyzer 22, to a radiation detector 23.

The ellipsometer 14 takes the information that it collects with the detector 23, and looks for changes introduced into the polarized components by the optical component 19. For example, the ellipsometer looks for changes in the amplitude of one component relative to the amplitude of the other component, and also looks for changes in the phase of one component relative to the phase of the other component. More specifically, for each of several different wavelengths within a range of interest, the ellipsometer 14 calculates a ratio of the amplitude of one of the polarized components relative to the amplitude of the other polarized component, as measured at the detector 23. Second, for each of the different wavelengths in the range, the ellipsometer determines a value representing a phase difference between two polarized components, as measured at the detector 23. All of this information is then supplied at 29 to a computer 31.

The computer 31 includes computer hardware in the form of a conventional, commercially-available computer system of the type commonly known as a personal computer. In the disclosed embodiment, the hardware is a personal computer obtained commercially from Dell Inc. of Round Rock, Tex. However, the computer 31 could alternatively contain any other suitable computer hardware. The hardware of computer 31 executes a software program that facilitates the design and modeling of optical coatings. In the disclosed embodiment, the software is a program obtained commercially under the tradename FILMWIZARD from Scientific Computing International of Carlsbad, Calif. However, the software could alternatively be any other suitable program. The computer 31 is operated by a human operator 32. The operator 32 is a person of ordinary skill in the art of coating design, who is familiar with use of the software executed by the computer 31.

The apparatus 10 includes a support 41, and a positioning mechanism 42 that supports the support 41 for pivotal movement about a pivot axis 43 that extends perpendicular to the plane of FIG. 1. The pivotal movement of the support 41 is indicated diagrammatically in FIG. 1 by a double-headed arrow 44. The positioning mechanism 42 is also capable of releasably holding the support 41 in any selected pivotal position.

Figure 2:
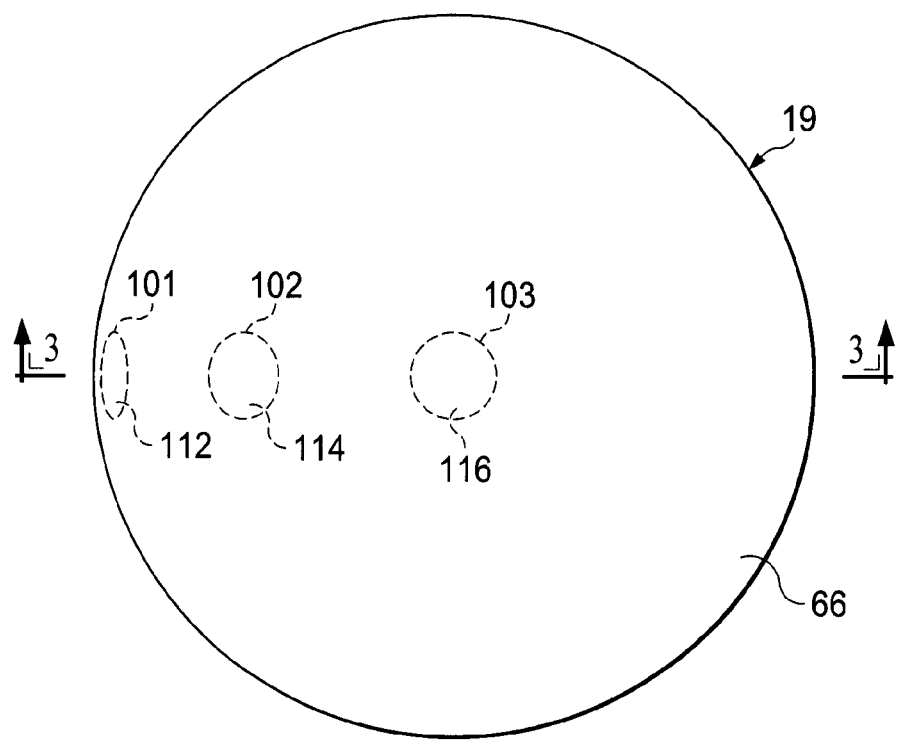
FIG. 2 is a diagrammatic front view of the optical component of FIG. 1, taken in the direction of arrow 56 in FIG. 1.
Figure 3:
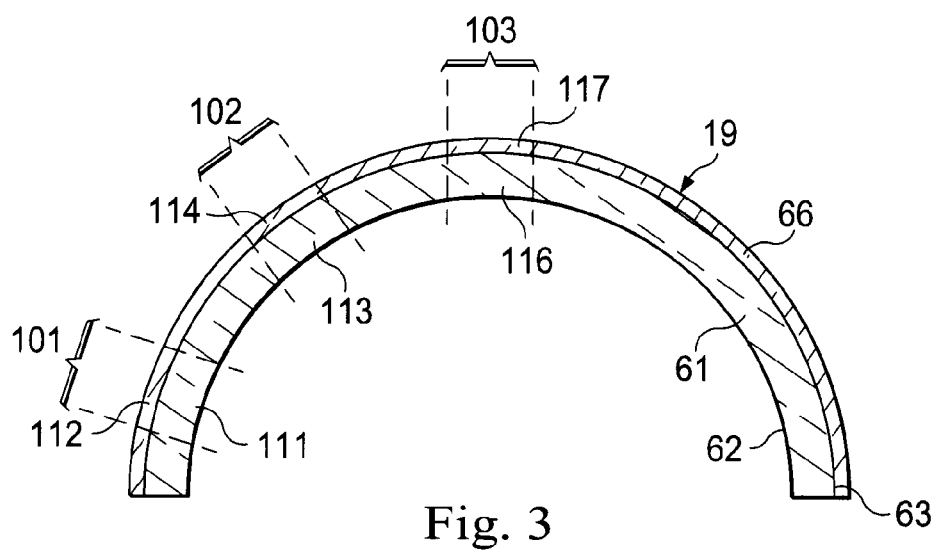
FIG. 3 is a diagrammatic sectional view taken along section line 3-3 in FIG. 2.

FIG. 2 is a diagrammatic front view of the optical component 19, taken in the direction of arrow 56 in FIG. 1. FIG. 3 is a diagrammatic sectional view of the optical component 19, taken along section line 3-3 in FIG. 2. As best seen in FIG. 3, the optical component 19 has a substrate 61, with a highly-curved concave inner surface 62, and a highly-curved concave outer surface 63. In the disclosed embodiment, the substrate 61 is made of zinc selenide (ZnSe), but it could alternatively be made of any other suitable material.

An optical coating 66 is provided on the curved outer surface 63 of the substrate 61. It would be possible for the coating 66 to be only a single layer of a single material. But in the disclosed embodiment, the coating 66 includes a plurality of different layers (not separately depicted), involving the use of one material for some layers, another material for other layers, and so forth. By interleaving different layers of different materials having different thicknesses, the coating 66 can be given certain desired optical and/or mechanical characteristics.

The layers of the coating may, for example, include silicon (Si) and silicon monoxide (SiO). It is possible that the multiple layers in the coating 66 would all have the same thickness. Typically, however, some layers are intentionally designed to be thicker or thinner than other layers. A separate consideration is that it is desirable for the thickness of each layer be relatively uniform throughout that layer. But as a practical matter, this can be difficult to achieve, especially where the outer surface 63 of the substrate 61 is highly curved. For example, one common coating technique is to place the substrate 61 in a not-illustrated vacuum chamber, with a conventional evaporation source disposed below the substrate 61, and then successively evaporate different materials with the evaporation source in order to successively form the layers of the coating 66. When the layers of a coating are formed in this manner, each layer of the resulting coating will tend to be thicker in its central region than in its peripheral edge region.

Different layers made of different materials may experience different degrees of variation in thickness. For example, a layer made of one material may have a peripheral edge region that is 35% thinner than its central region, whereas a different layer made of a different material may have an edge region that is 45% thinner than its central region. Since most or all layers in the coating 66 will be thinner in the edge region than in the central region, the coating will have an overall thickness in the edge region that is thinner than the overall thickness in the central region. In this regard, it is common for a coating to be 30% to 50% thinner in its edge region than in its central region. In the case of an optical component such as that illustrated at 19 in FIGS. 1-3, this variation in layer thicknesses and coating thickness can affect the optical performance of that component.

For example, assume hypothetically that the coating 66 is intended to pass radiation from a laser that has a wavelength of 1064 nm. More specifically, assume that the coating is configured to efficiently pass radiation within a waveband of 1040 nm to 1090 nm (where 1064 nm is approximately in the center of this waveband), that the coating has the proper thickness in its central region, and that the coating is about 35% thinner in its edge region that in its central region. Since the thickness changes by 35%, the effective operating range will also change by about 35%. For example, the coating may have the desired waveband of 1040 nm to 1090 nm in its central region, but a 35% variation in thickness could cause the effective operating waveband in the peripheral region of the coating to be about 676 nm to 709 nm (and it will be noted that the 1064 nm wavelength of interest is not within this altered waveband of 676 nm to 709 nm). Consequently, in order to evaluate a coating such as that shown at 66, it is desirable to be able to accurately measure characteristics of the coating, such as variations in thickness, optical characteristics, and/or density.

FIG. 3 shows three integral portions 101, 102 and 103 of the optical component 19 that have been selected to be sample portions. The sample portion 103 is located in the center of the optical component 19, the sample portion 101 is located near an outer edge of the component 19, and the sample portion 102 is located between the sample portions 101 and 103. Although FIG. 3 shows three sample portions 101-103, it would alternatively be possible to have a larger or smaller number of sample portions. Moreover, the locations of the sample portions could be different.

The sample portion 101 includes a substrate portion 111 that is part of the substrate 61, and a coating portion 112 that is part of the coating 66. The sample portion 102 includes a substrate portion 113 that is part of the substrate 61, and a coating portion 114 that is part of the coating 66. Similarly, the sample portion 103 includes a substrate portion 116 that is part of the substrate 61, and a coating portion 117 that is part of the coating 66.

Referring to FIGS. 1 and 3, the positioning mechanism 42 can selectively position and hold the optical component 19 so that the ellipsometer beam traveling along path 17 impinges on any selected one of the sample portions 101, 102 and 103. Initially, for example, the substrate 41 and the optical component 19 can be positioned so that the radiation impinges on the sample portion 101. Based on the reflected radiation received at the detector 23 from the path of travel 21, the ellipsometer determines, for each of several different wavelengths of interest, a ratio of the amplitudes of the two polarized components in the reflected radiation, and a phase difference between these two components. This information is provided at 29 to the computer 31.

The positioning mechanism 42 is then used to move the support 41 and the optical component 19 until the ellipsometer beam traveling along path 17 impinges on the sample portion 102 (FIG. 3). The ellipsometer 14 then again determines a ratio of amplitudes and also a phase difference for each of the different wavelengths, and supplies this information at 29 to the computer 31. Next, the positioning mechanism 42 positions the support 41 and the optical component 19 so that the ellipsometer beam traveling along path 17 impinges on the sample portion 103 (FIG. 3). The ellipsometer 14 then determines a ratio of amplitudes and a phase difference for each of the different wavelengths, and supplies this data at 29 to the computer 31.

The software running on the computer 31 can then, under direction of the operator 32, use the data received at 29 from the ellipsometer 14 to evaluate characteristics of the coating 66, such as thickness, optical properties, and material density. The software can also be used in a known manner to model potential adjustments to the design of the coating 19, in an attempt to improve and optimize the optical and mechanical characteristics of the multi-layer coating 66.

In FIG. 3, the coating 66 is provided on the convex outer surface 63 of the substrate 61. It is alternatively possible to provide a coating on the concave inner surface 62 of the substrate 61. However, if the inner surface 62 is sufficiently highly curved, it may be difficult or impossible to position the optical component so that the radiation beam from the ellipsometer 14 (FIG. 1) will have the clearance needed to travel without obstruction to and be reflected by some or all portions of the coating, and then travel without obstruction to the detector 23. Accordingly, a different approach can be used.

Figure 4:
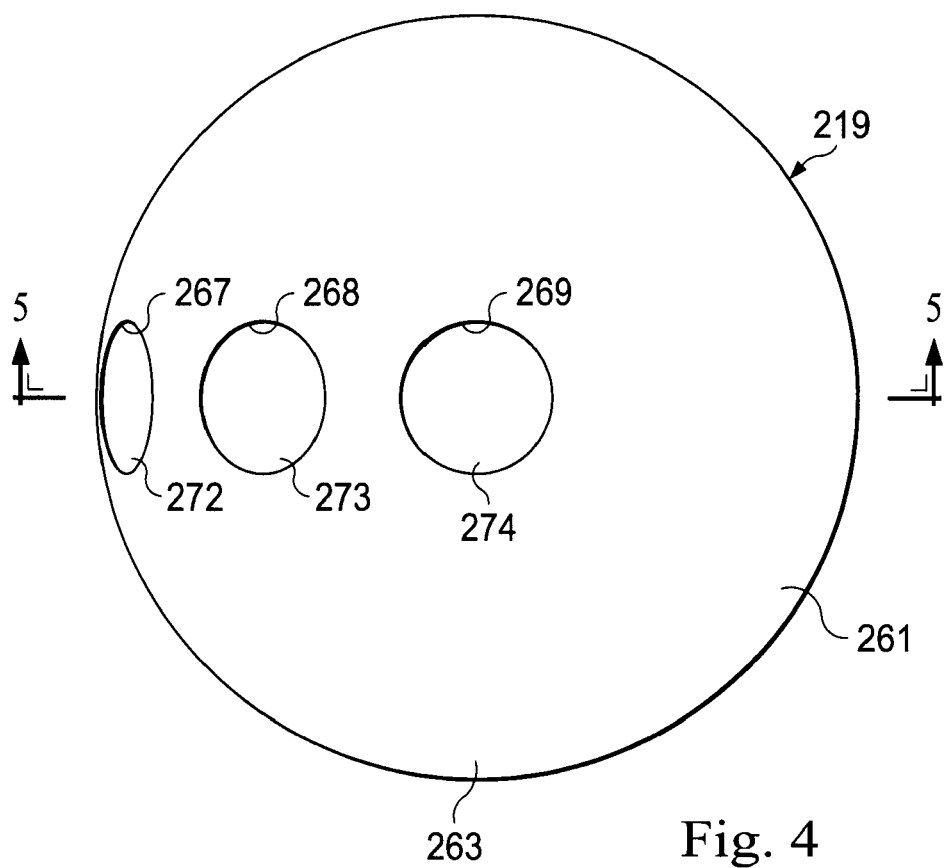
FIG. 4 is a diagrammatic front view of a "dummy" optical component.
Figure 5:
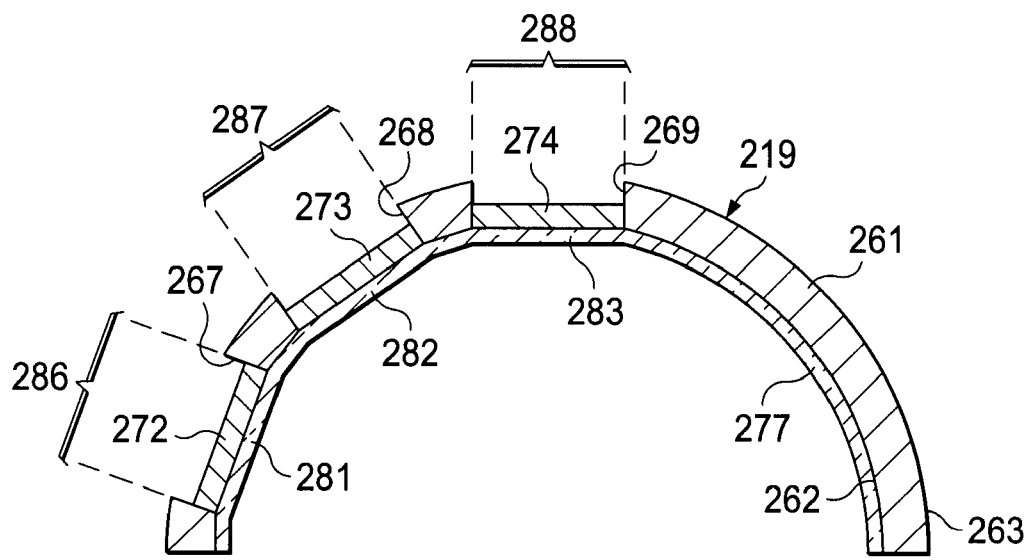
FIG. 5 is a diagrammatic sectional view taken along section line 5-5 in FIG. 4.

In this regard, FIG. 4 is a diagrammatic view that is similar to FIG. 2, but that shows a "dummy" optical component 219. FIG. 5 is a diagrammatic sectional view of the dummy optical component 219, taken along the section line 5-5 in FIG. 4. The component 219 includes a fixture or substrate 261 with a highly curved concave inner surface 262, and a highly curved convex outer surface 263. The surfaces 262 and 263 are equivalent in shape to the surfaces 62 and 63 in FIG. 3. The fixture 261 could optionally be made from an optical material such as zinc selenide. In the disclosed embodiment, the fixture 261 is made from stainless steel. But the fixture 261 could alternatively be made from any other suitable material, including but not limited to aluminum or regular steel.

The fixture 261 has three spaced circular openings 267, 268 and 269 that extend radially therethrough, and that have approximately equal diameters. The opening 269 is in the center of the fixture 261, the opening 267 is near a peripheral edge of the fixture 261, and the opening 268 is between the openings 267 and 269. The number and configuration of the openings 267-269 is exemplary. The number of openings could be larger or smaller, the shape of the openings could be different, and/or the relative positions of the openings could be different.

Three substrate portions 272, 273 and 274 are fixedly mounted in the openings 267, 268 and 269, respectively. The substrate portions 272-274 are approximately planar. Each substrate portion has a planar inner surface that, along its peripheral edge, is approximately flush with the inner surface 262 of the fixture 261. In the disclosed embodiment, the substrate portions 272-274 are each made from exactly the same material as the substrate of the actual optical component that will be coated. For example, if the substrate of the optical component is made from zinc selenide (ZnSe), then the substrate portions 272-274 are each made from zinc selenide. Alternatively, however, the substrate portions 272-274 could be made from some other suitable material.

Using known evaporative techniques, a multi-layer optical coating 277 is formed on the inner surface 262 of the fixture 261, and on the inner surfaces of each of the substrate portions 272-274. As a result, the substrate portion 272 has thereon a portion 281 of the coating 277, the substrate portion 273 has thereon a portion 282 of the coating 277, and the substrate portion 274 has thereon a portion 283 of the coating 277. The substrate portion 272 and the coating portion 281 together form a sample portion 286, the substrate portion 273 and the coating portion 282 together form a sample portion 287, and the substrate portion 274 and the coating portion 283 together form a sample portion 288. The sample portions 286-288 may alternatively be referred to as "witness pieces".

After the dummy component 219 of FIGS. 4 and 5 has been fabricated and coated, the sample portions 286, 287 and 288 are each removed from the fixture 261. The sample portion 272 is fixedly mounted on the support 41 of FIG. 1 (in place of the optical component 19), and then the ellipsometer 14 is used to analyze the coating portion 281 of the sample portion 286, in the same manner discussed above in association with the sample portions 101-103. The sample portion 286 is then removed from the support 41 and replaced with the sample portion 287, and the coating portion 282 of sample portion 287 is analyzed. Then, the sample portion 287 is removed from support 41 and replaced with the sample portion 288, and the coating portion 283 of sample portion 288 is analyzed. The resulting data is supplied at 29 to the computer 31, and is processed by the computer 31 and the operator 32 in a manner similar to that discussed above for the coating 66 of FIG. 1-3.

In the embodiment of FIG. 1, the support 41 can pivot about the axis 43, under control of the positioning mechanism 42. Alternatively, however, the support 41 and the positioning mechanism 42 could be omitted. The optical component 19 could initially be supported on a first non-movable and not-illustrated support that stationarily positions the optical component so that the ellipsometer beam impinges on the sample portion 101 (FIG. 3). Then, the optical component 19 could be stationarily supported on a second non-movable and not-illustrated support that stationarily positions the optical component 19 so that the ellipsometer beam impinges on the sample portion 102 (FIG. 3). Thereafter, the optical part 19 could be supported on a third non-movable and not-illustrated support that stationarily positions the optical component 19 so that the ellipsometer beam impinges on the sample portion 103.

The apparatus 10 of FIG. 1 permits measurement of variations in thickness, optical characteristics and material density across the radius of a component, with a high degree of accuracy and reliability. These measurements can then serve as a basis for improving and/or optimizing the optical and mechanical characteristics of a coating.

Although selected embodiments have been illustrated and described in detail, it should be understood that a variety of substitutions and alterations are possible without departing from the spirit and scope of the present invention, as defined by the claims that follow.

What is claimed is:

1. A method comprising: analyzing with an ellipsometer each of a plurality of sample portions that each include a substrate portion with a coating portion thereon, said substrate portions corresponding to respective spaced portions of a part with a curved surface, said analyzing including, for each said sample portion: directing onto said coating portion thereof a beam of radiation that includes first and second components having different polarizations; detecting energy of each of said first and second components reflected by the sample portion; and generating data that includes, for each of a plurality of different wavelengths, information regarding a change caused by the sample portion to a relationship between said first and second components.

2. A method according to claim 1, including forming a coating on said curved surface of said part before said analyzing, said substrate portions being respective portions of said part, and each having thereon a surface portion that is a section of said curved surface on said part, and said coating portion of each said sample portion being provided on said surface portion thereof and being a section of said coating on said part.

3. A method according to claim 2, including determining from said data a variation along said curved surface of a selected characteristic of said coating.

4. A method according to claim 3, wherein said selected characteristic is one of a thickness variation and a material density variation.

5. A method according to claim 1, including: fabricating said substrate portions of said sample portions as physically separate members; providing a fixture having a curved surface that is equivalent to said curved surface on said part, and that has a plurality of spaced recesses therein; supporting each of said substrate portions in a respective said recess before said analyzing; and thereafter forming a coating on said substrate portions and said curved surface of said fixture before said analyzing, said coating portions being respective sections of said coating.

6. A method according to claim 5, including determining from said data a variation along said curved surface on said fixture of a selected characteristic of said coating.

7. A method according to claim 6, wherein said selected characteristic is one of a thickness variation and a material density variation.

8. A method according to claim 1, wherein said generating of data is carried out in a manner so that said change to said relationship is a change to a ratio of the amplitude of one of said first and second components relative to the amplitude of the other thereof.

9. A method according to claim 1, wherein said generating of data is carried out in a manner so that said change to said relationship is a change to a phase difference between said first and second components.

10. A method according to claim 1, including configuring said beam of radiation so that, before reflection by each said sample portion, said first and second components thereof have substantially the same frequency and substantially the same amplitude, and are substantially in phase with each other.

11. A method according to claim 1, including configuring said curved surface to be highly curved.

12. A method according to claim 1, including selecting an optical component as said part.

* * * * *